United States Patent [19]

Szekely et al.

[11] 4,191,774
[45] Mar. 4, 1980

[54] NOVEL 17-AZA-PGF$_{2\alpha}$ DERIVATIVES AND PHARMACEUTICAL COMPOSITIONS CONTAINING THE SAME

[75] Inventors: Istvan Szekely; Gabor Kovacs; Sandor Virag; Matyas Szentivanyi, all of Budapest, Hungary

[73] Assignee: Chinoin Gyogyszer es Vegyeszeti Termekek Gyara R.T., Budapest, Hungary

[21] Appl. No.: 870,371

[22] Filed: Jan. 18, 1978

[51] Int. Cl.$^2$ ............... C07C 177/00; A61K 31/195; A61K 31/215

[52] U.S. Cl. .................... 424/300; 424/319; 560/115; 560/121; 562/503; 260/343.3 P; 260/340.73

[58] Field of Search ............... 560/115, 121; 562/503; 424/300, 319

[56] References Cited

U.S. PATENT DOCUMENTS 3,853,951   12/1974   Bernady et al. ..................... 260/465

FOREIGN PATENT DOCUMENTS 7206361  11/1972  Netherlands ............................. 560/121
1345934   2/1974  United Kingdom ..................... 560/121

OTHER PUBLICATIONS

Burger, Medicinal Chemistry, p. 77 (1960).

*Primary Examiner*—Robert Gerstl
*Attorney, Agent, or Firm*—Hubbell, Cohen, Stiefel & Gross

[57] ABSTRACT

N-Acylated 17-Aza-PGF$_{2\alpha}$ compounds have been prepared.

8 Claims, No Drawings

NOVEL 17-AZA-PGF$_{2\alpha}$ DERIVATIVES AND PHARMACEUTICAL COMPOSITIONS CONTAINING THE SAME The present invention relates to certain novel prostaglandin F$_{2\alpha}$ (PGF$_{2\alpha}$) derivatives and to a process for the production thereof.

More particularly, this invention relates to novel 17-aza-PGF$_{2\alpha}$ derivatives and isomers thereof and the pharmaceutically acceptable, non-toxic salts thereof.

The compounds of the present invention as described more fully hereinbelow, exclusive of the optically active antipodes thereof, exhibit valuable pharmaceutical activities and thus are useful as active ingredients of pharmaceutical compositions, which are also within the scope of the present invention.

The natural prostaglandins are derivatives of prostanoic acid which is a fatty acid of 20 carbon atoms containing a cyclopentane ring. It is well known that they are extremely potent in causing various biological responses and for this reason are useful for pharmacological purposes (Pharmacol. Rev. 20, 1/1968/). The compound PGF$_{2\alpha}$ can be employed in gynecology with especially excellent results (Belgian Pat. No. 738.177).

The compounds having a structure similar to that of prostaglandins, e.g. prostaglindin analogues are discussed in numerous publications. For example PGF$_{2\alpha}$ and PFE$_2$ analogues containing oxygen, sulfinyl or alkylimino groups in the 17-position, and optionally substituted aryl, benzyl or furfuryl groups on the terminal end of the lower side-chain as well as their contraceptive and hypotensive spasmolytic activities are disclosed in Dutch Pat. No. 7,206,361. Dutch Pat. No. 7,313,322 relates to prostaglandin analogues of similar structure containing monovalent hetero cyclic groups at the terminal end of the lower side-chain of prostaglandin.

It is the purpose of this invention to provide novel 17-aza-PGF$_{2\alpha}$ compounds of the formula:

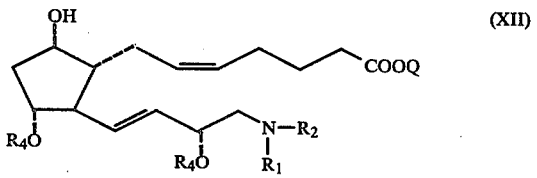

(XII)

or a racemate thereof, wherein
R$_1$ is hydrogen, lower alkanoyl, trihaloalkanoyl, optionally substituted benzoyl, lower alkoxycarbonyl, lower trihaloalkoxycarbonyl, or optionally substituted phenoxycarbonyl or benzyloxycarbonyl;
R$_2$ is hydrogen or alkyl of one to 4 carbon atoms(s);
R$_4$ is hydrogen or a protecting group;
Q is hydrogen, alkyl of one to 4 carbon atom(s) or a pharmaceutically acceptable non-toxic cation.

This invention relates not only to the optically active isomers of these compounds but to the racemate consisting of one of the optically active isomers and its mirror image.

The term "alkanoly" as used herein refers to straight or branched chained aliphatic acid radicals, having one to 4 carbon atom(s) (e.g., acetyl, propionyl, n-butyryl, etc.) The term "trihaloalkanoyl group" as used herein preferably means a trifluoroacetyl group. The term "optionally substituted benzoyl" is used herein to refer to benzoyl, which may be substituted by one or more substituents selected from the group consisting of halogen, alkyl, alkoxy, hydroxyl, nitro and amino. The term "lower alkoxycarbonyl" is used herein to identify, for example, methoxycarbonyl, ethoxycarbonyl, or butoxycarbonyl. The term "aryloxycarbonyl" as used herein preferably means phenoxycarbonyl, which may be substituted by one or more substituents selected from the group identified when defining the term "optionally substituted benzoyl". The term "trihaloalkoxycarbonyl" preferably means trichloroethoxycarbonyl.

With regard to R$_2$ and Q, examples of alkyl of one to 4 carbon atom(s) are preferably straight or branched chained saturated hydrocarbon groups of one to 4 carbon atom(s), e.g. methyl, ethyl, n-propyl, isopropyl, or n-butyl.

Examples of suitable pharmaceutically acceptable non-toxic salts of the compounds of the formula (XII) are sodium, potassium, calcium or ammonium salts, etc.

According to a further feature of the present invention, there is provided a process for the preparation of optically active compounds of the formula (XII), or a racemate thereof, wherein R$_1$, R$_2$, R$_4$ and Q are as defined above. The novel compounds of the present invention can be prepared by (a$_1$) reacting a compound of the formula:

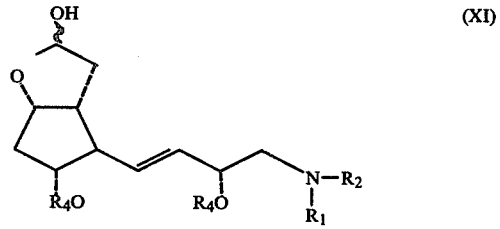

(XI)

wherein R$_1$ and R$_2$ are as defined above and R$_4$ is hydrogen or a protecting group conventional in the chemistry of prostaglandins, with a phosphorane prepared from a triphenyl-(4-carboxybutyl)-phosphonium salt; or (a$_2$) reducing a compound of the formula:

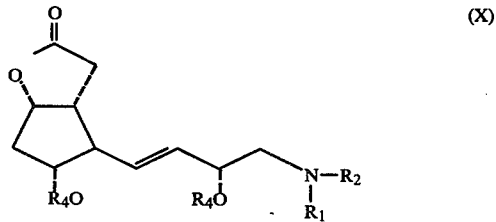

(X)

wherein R$_1$, R$_2$ and R$_4$ are as defined above, with a complex metal hydride, and subsequently reacting a compound of the formula (XI) obtained with a phosphorane prepared from a triphenyl-(4-carboxybutyl)-phosphonium salt; or (a$_3$) reducing a compound of the formula:

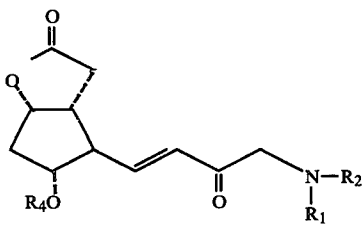

(VIII)

wherein $R_1$, $R_2$ and $R_4$ are as defined above, with a complex borohydride, subsequently reducing a compound of the formula (X), obtained with a complex metal hydride, and finally reacting a compound of the formula (XI) obtained with a phosphorane prepared from a triphenyl (4-carboxybutyl)-phosphonium salt; and optionally carrying out one or more of the following steps:

(1) introducing an $R_4$ protecting group into a compound of the formulae (X) or (XI) or splitting off an $R_4$ protecting group from a compound of the formulae (VIII), (IX)

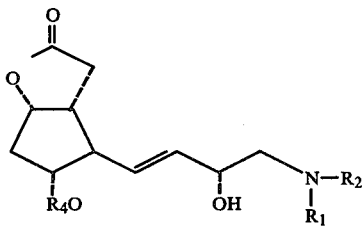

(IX)

(X) or (XI);

(2) if in a compound of the formula (XII) obtained, $R_4$ represents a protecting group, splitting off this group;

(3) transforming a compound of the formula (XII) obtained wherein $R_1$ is optionally substituted phenoxycarbonyl, benzyloxycarbonyl, alkoxycarbonyl or trihaloalkoxycarbonyl, into a corresponding compound of the formula (XII), wherein $R_1$ is hydrogen, by hydrolysis carried out in an acidic medium;

(4) transforming a compound of the formula (XII) obtained wherein $R_1$ is hydrogen, into a corresponding compound of the formula (XII), wherein $R_1$ is lower alkanoyl or optionally substituted benzoyl, by reacting it with an agent suitable for introducing a lower alkanoyl or optionally substituted benzoyl into the molecule;

(5) transforming a compound of the formula (XII) obtained, wherein O is hydrogen, into a corresponding compound of the formula (XII), wherein O is a lower alkyl;

(6) transforming a compound of the formula (XII) obtained, wherein O is hydrogen, into a non-toxic salt thereof;

(7) separating a compound of the formulae (IX), (X), (XI) or (XII) into the epimers thereof.

The novel compounds prepared according to this invention are much more effective than natural $PGF_{2\alpha}$ and combine the typical effects of prostaglandins with an α-adrenergic stimulating effect.

According to a preferred embodiment of the process according to the invention compounds of the formula (XII), wherein $R_1$ is acetyl, $R_2$ is n-propyl and O is hydrogen, are prepared.

In the starting compounds of the formulas (VIII), (X) or (XI) $R_4$ is hydrogen or a protecting group. As protecting groups all the protecting groups generally used in the chemistry of prostaglandins can be employed. Thus $R_4$ may be a protecting group stable against alkaline treatment and easily removable in an acidic medium. Examples of the suitable protecting groups are: tetrahydropyranyl, or trialkylsilyl, e.g. trimethylsilyl or triethylsilyl etc. $R_4$ may be p-phenyl-benzoyl as well.

The protecting groups are introduced into the molecule by techniques known per se.

For instance, a tetrahydropyranyl group can be introduced by reacting a compound containing a free hydroxyl with 3,4-dihydro-2H-pyran. The reaction is conducted in a solvent or in the absence of a solvent, in the presence of traces of an acid catalyst. Suitable solvents for this reaction are chlorinated hydrocarbons (e.g. dichloromethane) and as an acid catalyst, traces of phosphorous oxychloride or p-toluene-sulphochloride can be used.

The trialkylsilyl protecting group can be introduced into the molecule by using trialkylsilyl chloride. The reaction is preferably effected in the presence of an acid binding agent, for instance pyridine.

The p-phenyl-benzoyl protecting group can be derived from p-phenyl-benzoyl chloride. This protecting group can be introduced into the compounds of the formulae (X) and (XI) as well.

The tetrahydropyranyl and trialkylsilyl protecting groups can be split off by acid treatment when the desired reaction is completed. Preferably an aqueous solution of acetic acid is used for this purpose.

The p-phenyl-benzoyl group represented by $R_4$ is automatically split off under the conditions of the Wittig-reaction. If the p-phenyl-benzoyl group is to be eliminated during an earlier phase of the process (e.g. from the compounds of the formula /IX/) it can be removed by potassium carbonate, in a methanolic medium.

Compounds of the formula (XI) can be transformed into the corresponding compounds of the formula (XII) by the Wittig-reaction, in a manner known per se. As the Wittig-reactant, a phosphorane prepared from a triphenyl-(4-carboxybutyl)-phosphonium salt can be employed. In a preferred embodiment a dimethyl sulphoxide solution of dimsyl-sodium is prepared by reacting dimethyl sulphoxide and sodium hydride, to which triphenyl-(4-carboxybutyl)-phosphonium bromide is then added, followed by the addition of a compound of the formula (XI). The compound of the formula (XII) prepared may be isolated by using any of the known methods, preferably by column chromatography (carried out for example on silica gel).

Compounds of the formula (XI) may be prepared by reducing compounds of the formula (X). Reduction is carried out by methods generally known in the chemistry of prostaglandins. Reduction is preferably effected with diisobutyl aluminum hydride, in an aprotic solvent (e.g. toluene) at a temperature between 0° and −100° C., preferably between −70° to −80° C. Alternatively, the two hydroxyls of the compounds of the formula (X), wherein $R_4$ is hydrogen can be blocked by suitable protecting groups (e.g. tetrahydropyranyl). The reaction is performed as described above.

The compounds of the formula (X) are prepared by reducing the corresponding compounds of the formula (VIII). As reducing agnets complex borohydrides are used. For example zinc-borohydride or sodium-borohydride can be used for this purpose in an ethereal medium. As a result of this reduction (S)- and (R)-isomers are obtained, depending on the configuration of the 15-hydroxyl group. When the reduction is carried out with zinc-borohydride, (S)-isomer, corresponding to the natural prostaglandin structure and (R)-isomer are obtained in a proportion of 1:1.

According to a preferred embodiment, reduction is effected with lithium-tri-(sec. butyl)-borohydride, when about 80% of the product is the desired (S)-isomer, while the (R)-isomer is obtained only in a quantity of about 20%. The reduction is conducted in an ethereal medium, preferably in a mixture of tetrahydrofuran and ether, preferably at a temperature below $-100°$ C. A temperature of about $-130°$ C. is especially preferred, which can be ensured by using a methyl-cyclohexane nitrogen cooling bath. The compounds of the formula (IX) (S)- and (R)-isomers, if desired, are separated by conventional means, generally by column chromatography. This step can however be omitted—especially if the reduction is performed by using lithium-tri-(sec.-butyl)-borohydride—since the end product is isolated by column chromatography anyway, which makes possible the separation of the non-desired isomer present in a small quantity.

From the compounds of the general formula (IX) or (X), wherein $R_4$ is p-phenyl-benzoyl the p-phenyl-benzoyl protecting group can be removed by an alkaline treatment, preferably with potassium carbonate.

Compounds of the formula (XII), wherein $R_1$ is aryloxycarbonyl, alkoxycarbonyl or trihaloalkoxycarbonyl can be transformed into the corresponding compounds of the formula (XII), wherein $R_1$ is hydrogen. The acid treatment is preferably accomplished in a hydrogen bromide-glacial acetic acid mixture.

The compounds of the formula (XII) obtained, wherein $R_1$ is hydrogen can be alkanoylated or benzoylated with reactants suitable to introduce lower alkanoyl or optionally substituted benzoyl into the molecule. Example of suitable reactants are acetyl chloride, acetic anhydride or benzoyl chloride.

The compound of the formula (XII) obtained, wherein O is hydrogen can be transformed into the corresponding esters, wherein O is a lower alkyl. Esterification is carried out in a known manner, e.g. with diazomethane.

The compounds of the invention are transformed into the corresponding salts thereof by conventional means, by interaction of the acid with a corresponding base.

Starting compounds of the formula (VIII) are novel and are prepared by using a method described hereinbelow. An amine of the formula $R_2$—$NH_2$ (I) is acylated with an acid chloride of the formula R/Cl (II), in the presence of an acid binding agent in a manner known per se. In the formula (II) $R_1'$ is alkanoyl, trihaloalkanoyl or optionally substituted benzoyl. If compounds of the formula

wherein $R_1$ is alkoxycarbonyl, trihaloalkoxycarbonyl or aralkoxycarbonyl, are to be prepared, an amine of the formula (I) is reacted with a chloroformic acid alkyl- or arylester.

The acid proton of the compound of the formula (III) is replaced by an alkali metal atom by means of strong bases, e.g., an alkyl-lithium, preferably butyl-lithium or an alkali metal hydride, to prepare a compound of the formula

wherein Me is an alkali metal and $R_1$ and $R_2$ are as defined above. This is then further reacted with a phosphorane of the formula

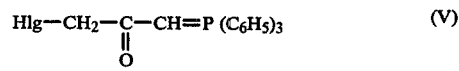

wherein Hlg is halogen. The reaction is accomplished in a known manner. The compound of the formula

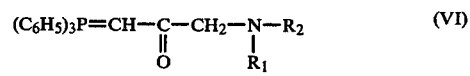

prepared in this way, wherein $R_1$ and $R_2$ are as defined above, is reacted with a Corey-aldehyde of the formula

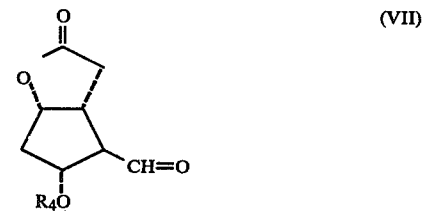

wherein $R_4$ is as defined above, in a manner known per se. The Corey-aldehyde of the formula (VII) is preferably prepared — due to its instable character—in situ, by oxidizing a corresponding alcohol of the formula

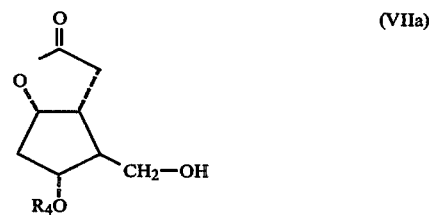

The obtained compound of the formula (VIII) is separated from the triphenyl-phosphine-oxide in a manner described with reference to the Wittig-reaction. (Column chromatography).

The compounds of the formula (XII) exhibit valuable pharmaceutical activities. It has been proved by biochemical studies carried out on a rat womb kept in Krebs-Ringer bicarbonate solution that the instant compounds show approximately the same activity as $PGF_{2\alpha}$. They cause a stronger contraction in the presence of adrenergic blocking agents.

They increase the lypolysis of epidermic fatty tissues of rats. In this respect they have a stronger effect than natural catecholamines.

In view of the above results, the compounds have a double effect. They may act either as a catecholamine or as a prostaglandin, depending on the organs treated and on the medium used during the treatment. When catecholamine inhibitors are employed the prostaglandin character will be predominant. Therapeutically the effect excerted on fatty tissues and smooth muscles, preferably on womb is of special importance.

The compounds of this invention are useful in regulating gastric secretion and in dispergating platelet clogs responsible for thrombosis.

The compounds of the present invention are administeredpreferably at a dose level in the range of 0.1 μg to 5 μg/kg/min in form of an infusion. The same doses can also be used for regulating the metabolism of fatty acids.

The smooth muscle stimulating effect of the compounds can be used to potentiate known smooth muscle stimulating agents, at a dose level of 0.001 to 25 μg/kg. On the other hand, these compounds are useful in mammals, including humans, for procured abortion, starting labor, and to control menstruation or expand cervix to permit intravaginal, intrauterine or intravenous administration. For the above purposes the compounds of the invention are administered in unit doses of 1 μug to 20 mg or intravenously at an infusion rate of 5 to 50 mg./kg./hour. The exact dose is a function of the age, condition and weight of the person or animal to be treated.

The compounds encompassed by formula (VII) and pharmaceutically acceptable, non-toxic salts thereof may be formulated into pharmaceutical compositions by the conventional techniques of pharmaceutical industry. The pharmaceutically administrable compositions can be in solid (capsules, tablets); semi-solid (e.g. ointments); or liquid (e.g. solutions, suspensions or emulsions) forms. Administration of the compositions can preferably be parenterally or vaginally. The compositions will include a conventional solid or liquid pharmaceutical carrier or excipient (e.g. water, aqueous sodium acetate solution, normal saline solution).

The following Examples illustrate the invention but are not intended to limit its scope.

EXAMPLE 1

12 g. of a sodium hydride suspension (0.1 mole; 20% suspension in paraffin oil) are weighed into a 1000-ml. 4-necked round bottomed flask equipped with a cooler, stirrer, thermometer and a dropping funnel under nitrogen astmosphere. 358 ml. of dry dimethoxy ethane are then added, and to the obtained suspension, a solution of 10.1 g. (0.1 moles) of N-propyl-acetamide in 50 ml. of dry dimethoxy ethane is poured at room temperature, under stirring. The mixture is refluxed for two hours, cooled to room temperature when the sodium salt of the amide prepared is obtained in form of a gel-like precipitate. 35.3 g. (0.1 mole) of triphenyl-chloroacetonyl-phosphorane suspended in 50 ml. of dry dimethoxy ethane are added to the reaction mixture.

It is stirred for a further two hours to slowly dissolve the amide salt precipitate. Dimethoxy ethane is distilled off, the residue is taken up in ethyl acetate, washed with water and subsequently with brine, dried over sodium sulphate and evaporated.

44 to 46 g. of crude triphenyl (N-propyl-acetylamino)-acetonyl phosphorane are obtained. Melting point (after recrystallization from a tetrahydrofurane/ether mixture): 147° to 148° C.

Yield: 34.7 g. (83%) IR: 3080, 1640, 750, 720, 695 cm$^{-1}$ NMR (CDCl$_3$) δ=7.4–8.0 (m, 15H, aromatic), δ=3.65–4.25 (compl. 3H, PC$\underline{H}$+COC$\underline{H}_2$N), δ=3.52 (t, 2H, NC$\underline{H}_2$, J=7Hz), δ=2.17 (s, 3H, COC$\underline{H}_3$), δ=1.1–2.0 (m, 2H, C$\underline{H}_2$CH$_3$) δ=0.9 (b, 3H, CH$_2$C$\underline{H}_3$)

EXAMPLE 2

290 ml. of a 0.049 g./ml. solution of chlorine in carbon tetrachloride (0.2 moles) are weighed into a 2000-ml. 4-necked round bottomed flask fitted with a dropping funnel, stirrer, thermometer and a calcium chloride filled drying tube. The solution is cooled in a chloroform/dry-ice bath to −10° C. and 24.8 g. (0.2 moles) of thioanisole in 200 ml. of dry dichloromethane are added at the same temperature. The mixture is stirred for 30 minutes, cooled to −25° C. and treated dropwise with 35.2 g. (0.1 mole) of (−)-3,3aβ-4,5,6,6aβ-hexahydro-4β-hydroxymethyl-5α-(4-phenyl-benzoyloxy)-2-oxo-cyclopenta[b]furane. When the addition is completed, the reaction mixture is stirred at the same temperature for two hours.

40.4 g (0.4 moles) of triethyl amine in 200 ml. of dichloromethane are then added dropwise, and the temperature is allowed to rise to room temperature. The reaction mixture is then poured onto 1 lit. of 1 N aqueous hydrochloric acid solution. The aqueous phase is separated, and the organic phase is washed with water, dried over magnesium sulphate and evaporated under reduced pressure.

After solidifying, the crude product is suspended in cool ether and the white crystals that form are filtered off. 26.4 g. of (−)-3,3aβ,4,5,6,6aβ-hexahydro-4β-formyl-5α-(4-phenyl-benzoyloxy)-2-oxo-2H-cyclopenta[b]furane are obtained.

The compound of the formula (VII) formed above is added to a solution of 34.2 g. (0.082 moles) of triphenyl-(N-propylacetylamino)-acetonyl phosphorane in 100 ml. of dichloromethane, in a 250 ml. round bottomed flask. If desired, 0.01 mole of butyric acid catalyst can be added to the reaction mixture. The solution is allowed to stand overnight, diluted with 200 ml. of dichloromethane and then washed with 200 ml. of a 1 N hydrochloric acid solution of 0° C. and subsequently with 100 ml. of water. The organic phase is dried and evaporated. 63 g. of (−)-3,3aβ,4,5,6,6aβ-hexahydro-4β-[3-oxo-4-(N-propyl-acetylamino)-1-transbuthenyl]-5α-(4-phenyl-benzoyloxy)-2-oxo-2H-cyclopenta[b]furane are obtained, in the form of a yellow oil.

Yield: 28.9 g. (59.2%); R$_f$=0.3 (5% methanol/ethyl acetate) IR (liquid film): 3080, 2900, 1780, 1720, 1700, 1650, 975, 755 and 695 cm$^{-1}$. NMR (CDCl$_3$): δ=7.2–8.2 (m, 9H aromatic protons), δ=6.2–7.2 (d+dd, 2H, trans olefin protons, J=36 Hz), γ=4.9–55 (m, 2H, OC$\underline{H}$), δ=4.3 (s, 2H, COC$\underline{H}_2$N), δ=3.0–3.4 (m ,2H, C$\underline{H}_2$N), δ=2.13 (s, 3H, COC$\underline{H}_3$), δ=0.9 (t, 3H, CH$_2$C$\underline{H}_3$.

EXAMPLE 3

A 250 ml. dry 4-necked round bottomed flask fitted with a stirrer, resistance thermometer and gas connection, thetrahydrofurane bubbler and a silicon gum cap is charged with 30 ml. (0.03 moles) of Li-selectride [litihium-tri(sec.-butyl)-borohydride in tetrahydrofurane (1 mole)], 160 ml. of dry ether and 20 ml. of dry tetrahydrofurane. The solution is cooled in a slow argon flow (with methyl-cyclohexane or ether/petroleum ether and a liquid nitrogen bath) to −130° C. To the Li-selectride solution through the silicon gum cap there are injected 4.9 g. (0.01 mole) of (−)-3,3aβ,4,5,6,6aβ-hexahydro-4β-[3-oxo-4-(N-propylacetylamino)-1-trans-buthenyl]-5α-(4-phenyl-benzoyloxy)-2-oxo-2H- cyclopenta[b]furane taken up in 20 ml. of dry tetrahydrofurane within 30 minutes, under vigorous stirring. The reaction mixture is stirred at −127° C. to −130° C. for one hour. The reaction is monitored by layer chromatography (5% solution of methanol/ethylacetate). $R_f$ for the compound of formula (VIII)=0.3; $R_f$ for the compound of formula (IX)=0.27.

The excess reducing agent is decomposed with 5 ml. of methanol, and the reaction mixture is poured onto 500 ml. of a 1 M aqueous sodium bicarbonate solution, while it cools. The organic phase is separated and shaken with three 100-ml. portions of ethyl acetate. The combined organic phases are washed with brine, dried over sodium sulphate, concentrated in vacuo to 100 ml., diluted with 200 ml. of petroleum ether and the solution is subjected to silica gel chromatography (200 g.; grain size: 0.063 to 0.2 mm.). The alkali metal boranes are washed with a 2:1 mixture of petroleum ether and ethyl acetate, and (−)-3,3aβ,4,5,6,6aβ-hexahydro-2-oxo-4β-[(3S)-3-hydroxy-4-(N-propyl-acetylamino)-trans-1-butenyl]-5α-(4-phenyl-benzoyloxy)-2H-cyclopenta[b]furane is eluted with a 5% methanol/ethyl acetate mixture.

The fractions corresponding to $R_f$=0.27 (5% methanol/ethyl acetate) are pooled and evaporated.

Yield: 3.1 g. (63.3%), yellow oil 2nd crop from a transitional fraction: 0.4 g. (8.15%) Total yield: 3.5 g. (71.5%)

$R_f$=0.27 (5% methanol/ethyl acetate) IR (liquid film): 3450, 3080, 2950, 2980, 1770, 1725, 750, 700 cm$^{-1}$. NMR (CDCl$_3$): δ=7.4–8.3 (m, 9H, aromatic protons), δ=5.8 (m, 2H, olefin protons), δ=5–5.5 (m, 2H, OCH), γ=4.45 (m, 1H, OCH, allyl), δ=3–3.6 (m, 4H, NCH$_2$), δ=2.13 (s, 3H, COCH$_3$), δ=0.9 (t, 3H, J=6Hz, CH$_2$CH$_3$)

EXAMPLE 4

In a 250-ml. round bottomed flask there are dissolved 4.9 g. (0.01 mole) of (−)-3,3aβ,4,5,6,6aβ-hexahydro-2-oxo-4β-[(3S)-3-hydroxy-4-(N-propyl-acetylamino)-trans-1-buthenyl]-5α-(4-phenyl-benzoyloxy)-2H-cyclopenta[b]furane in 50 ml. of dry methanol and 1.5 g. (0.011 moles) of burnt out and powdered potassium carbonate are added. The flask is fitted with a calcium chloride filled drying tube and the suspension is stirred with a magnetic stirrer at room temperature.

The course of the reaction is monitored with layer chromatography (5% methanol/ethyl acetate) which indicates that the reaction is completed after one hour. $R_f$ for a compound of formula (IX)=0.27; $R_f$ for a compound of formula (X)=0.05; $R_f$ for 4-phenyl-benzoic acid methylester=0.95.

The reaction mixture is neutralized with 1 M hydrochloric acid in methanol to pH 6 and the methanol is subsequently distilled off in vacuo. The residue containing more components and solid and liquid phases is taken up in 100 ml. of a 2:1 mixture of petroleum ether and ethyl acetate and poured onto a silica gel column. The 4-phenylbenzoic acid methylester is eluted with a 2:1 mixture of petroleum ether and ethyl acetate, while the (−)-3,3aβ,4,5,6,6aβ-hexahydro-2-oxo-5α-hydroxy-4β-[(3S)-3-hydroxy-4-(N-propylacetylamino)-trans-1-butenyl]-2H-cyclopenta[b]furane is eluted with a 10% methanol/ethyl acetate mixture.

Yield: 2.93 g. (93.4%), yellow oil. $R_f$: 0.33 (10% methanol/ethyl acetate) IR (liquid film): 3450, 2950, 2980, 1775, 1635 cm$^{-1}$. NMR (CDCl$_3$): δ=5.65 (m, 2H, olefin protons), δ=5.0 (m, 1H, OCH lactone), δ=4.35 (m, 1H, OCH allyl proton), δ=4.10 (m, 1H, OCH), interchangeable OH protons 2H; δ=3.1–3.5 (m, 4H, NCH$_2$), δ=2.13 (s, 3H, COCH$_3$), δ=0.9 (t, 3H, CH$_2$CH$_3$, J=7Hz).

EXAMPLE 5

Into a 250 ml. dry, four-necked round bottomed flask equipped with a stirrer, thermometer, gas connection, dropping funnel and a dry tetrahydrofurane bubbler, a solution of 3.1 g. (0.01 mole) of (−)-3,3aβ,4,5,6,6aβ-hexahydro-2-oxo-5α-hydroxy-4β-[(3S)-3-hydroxy-4-(N-propylacetylamino)-trans-1-butenyl)]-2H-cyclopenta[b]furane in 70 ml. of dry tetrahydrofurane is added, the flask is flushed with dry argon and cooled to −78° C. in an acetone dry-ice bath, in a slow argon flow.

6.4 g. (0.046 moles) of diisobutyl-aluminum hydride in 70 ml of dry toluene are added to the cooled solution over 30 minutes, under vigorous stirring. The gas evolution ceases before the addition is finished. When the addition is completed, the reaction mixture is stirred at −78° C. for one hour. The reaction is monitored by layer chromatography, which indicates that at the end of the one hour stirring period (after an ethyl acetate-/ammonium chloride microprocessing) the reaction is completed.

The reaction mixture is decomposed with 10 ml. of 2 N sodium hydrogen sulphate solution. The bath is then removed and the temperature of the mixture is allowed to rise to 0° C. The pH of the mixture is adjusted to 3 to 4 with a 2 M sodium hydrogen sulphate solution. The organic phase is separated in a separating funnel. The aqueous phase is shaken with six 50-ml. portions of ethyl acetate, the combined organic phases dried over sodium sulphate and evaporated under reduced pressure. 3 g. (97% of crude (−)-3,3aβ,4,5,6,6aβ-hexahydro-2,5α-dihydroxy-4β-[(3S)-3-hydroxy-4-(N-propyl-acetylamino)-trans-1butenyl]-2H-cyclopenta[b]furane are obtained as a yellow oil.

A sample for analysis is prepared on a silica gel column, using 20% methanol/ethyl acetate mixture; the fractions corresponding to $R_f$=0.095 (ethyl acetate/acetic acid 20:4) are pooled.

IR (liquid film): 3400, 2950, 2975, 1630, 1010, 1060, 1070, 1110 cm$^{-1}$. NMR (CDCl$_3$): δ=5.65 (m, 3H, 2 olefin proton+OCHO) δ=4–4.7 (m, 3H, OCH allyl, OCH 5β, OCH 6aβ) interchangeable protons 3H, δ=3.1–3.65 (m, 4H, NCH$_2$), δ=2.13 (s, 3H, COCH$_3$), δ=0.9 (t, 3H, CH$_2$CH$_3$).

EXAMPLE 6

Into a 500-ml. 4-necked round bottomed flask containing a magnetic stirring bar and fitted with a gas connection, silicon gum cap, vacuum connection and ground stopper. 10.8 g (0.09 moles) of a 20% sodium hydride suspension in paraffine oil are weighed, after flushing with argon. 10 ml. of dry petroleum ether are then injected into the suspension.

The mixture is suspended with the magnetic stirrer, allowed to settle and the petroleum ether oily phase is drawn up with a syringe. The above procedure is repeated twice and the remaining petroleum ether is removed in vacuo.

To the sodium hydride released from the oil 150 ml. of dry dimethyl sulphoxide are added, and the flask is equipped with a thermometer, dimethyl sulphoxide bubbler wherein it is flushed with argon. The suspension is then slowly heated up to 75° C. in an oil bath. Starting from α° C. an ever increasing hydrogen evolution is observed, which ceases within about 30 minutes. The pale yellow solution obtained is stirred at 70° to 75° C. for approximately 60 minutes, cooled to 15° to 20° C. and 20 g. (0.045 moles) of triphenyl-(4-carboxy-butyl)-phosphonium bromide are added in four portions the measuring container being rinsed with 50 ml. of dry dimethyl sulphoxide. The phosphorane formation is immediately indicated by the appearance of a red color. The solution is stirred at room temperature for 30 minutes, and 3.12 g. (0.01 mole) of (−)-3,3aβ,4,5,6,6aβ-hexahydro-2,5α-dihydroxy-4β-[(3S)-3-hydroxy-4-(N-propyl-acetylamino)-trans-1-butenyl]-2H-cyclopenta[b]furane are then added to the reaction mixture dissolved in 100 ml. of dry dimethyl sulphoxide. The mixture is stirred at room temperature. After 18 hours, the reaction is completed as indicated by thin layer chromatography (after decomposing the sample taken from the reaction mixture with ethyl acetate and sodium hydrogensulphate). For a compound of formula (XII) $R_f$ =0.23; and for a compound of the formula (XI) $R_f$ =0.09 (ethyl acetate/acetic acid 20:4).

The reaction mixture is poured onto the mixture of 400 ml. of 2 M sodium hydrogensulphate, 100 ml. of ice water and 150 ml. of ethyl acetate. The phases are shaken in a separating funnel, the organic phase is separated and the aqueous phase (pH=1) extracted with six 100-ml. portions of ethyl acetate. The organic phases are cooled combined and washed with three 50-ml. portions of sodium hydroxide at 0° C. The alkaline extracts are combined, 100 ml. of ethyl acetate are added and the solution is acidified to pH 3 by careful addition of 2 M sodium hydrogensulphate at 0° C. The organic phase is dried over sodium sulphate and evaporated to yield 3.7 g. crude product in the form of a dark-brown oil.

The crude product is chromatographed on 300 g. of silica gel using a 20:4 mixture of ethyl acetate and acetic acid.

Products corresponding to a spot at $R_f$ =0.62 in a methanol/ethyl-acetate/acetic acid 5:20:4 mixture are collected. Yield: 2.2. g (6.25%) (+)-9α,11α,15(S)-trihydroxy-16(N-propyl-acetylamino)-17,18,19-20-tetranor-5-cis-13-trans-prostadienic acid obtained is contaminated with the traces of (N-acetyl-7-aza-PGF$_{2\alpha}$)-acetic acid. It is further purified by a repeated column chromatography carried out on 100 g. of silica gel, using acetone as an eluting agent.

As a main fraction 1.73 g. (78% calculated for a chromatographed crude product) of a yellow viscous oil is obtained. $R_f$=0.62 (methanol/ethyl acetate/acetic acid 5:20:4) NMR (CDCl$_3$): δ=5.6 and δ=5.4 (m, 2H+2H, trans and cis olefin protons), δ=3.9; 4.15 and 4.3 (1–1m, 3H, 9-OC$\underline{H}$, 11-OCH and 15-allyl OC$\underline{H}$ protons), interchangeable protons. δ=3.15–3.6 (m, 4H, NCH$_2$), δ=2.13 (s, 3H, COC$\underline{H}_3$ δ=0.95 (t, 3H, CH$_2$CH$_3$, δ=7Hz). IR (liquid film): 3400, 1730, 1630, 1445, 1260, 1025, 960 cm$^{-1}$. Specific rotation: [α]$_D^{20}$ = +19 (±2) (c=1.2; tetrahydrofuran)

Example 7

In a similar manner as described in Example 1 but using 19.3 g. (0.1 mole) of N-propyl-benzylurethane instead of N-propyl-acetamide there are obtained 39.7 g. (78%) triphenyl-(N-propyl-benzyloxycarbonylamino)-acetonylphosphorane.

Melting point: 111° C. to 112° C; IR (KBr): 1705, 1520, 1390, 1230, 1100, 740, 705, 695 cm$^{-1}$. NMR (CDCl$_3$): δ=7.1–8 (m, 20H, aromatic protons), δ=5.2 (s, OC$\underline{H}_2$, 2H) δ=3.9–4.8 (m, 3H, PC$\underline{H}$ +COCH$_2$N).

Example 8

In a similar manner as described in Example 1 but substituting 13.1 g. (0.1 mole) of N-propyl-ethyl-urethane for N-propyl-acetamine there are obtained 35.1 g. (78.3%) of triphenyl-(N-propyl-ethoxycarbonylamino)-acetonylphosphorane.

Melting point: 92° to 94° C.; IR (KBr): 1695, 1580, 1390, 1240, 1100, 750, 715 and 695 cm$^{-1}$. NMR (CDCl$_3$): δ=7–7.9 (m, 15H, aromatic protons), δ=3.9–4.6 (m, 5H, PC$\underline{H}$+COC$\underline{H}_2$N+OC$\underline{H}_2$) quartett, 4.1, J=8Hz).

Example 9

In a similar manner as described in Example 2 but substituting 41.8 g. (0.082 moles) of triphenyl-(N-propylbenzyloxycarbonylamino)-acetonyl-phosphorane for triphenyl-(N-propyl-acetylamino)-acetonyl-phosphorane there are obtained 35.9 g. (63%) of (−)-3,3aβ-4,5,6,6aβ-hexahydro-2-oxo-4β-[3-oxo-4-(N-propyl-benzyloxycarbonyl-amino)-transbuthenyl]-5α-(4-phenyl-benzoyloxy)-2H-cyclopenta[b]furane. Rf =0.3 (petroleum ether/ethyl acetate 1:1) and 0.85 (ethyl acetate) NMR (CDCl$_3$): δ=7.4–8.3 (m, 14H, aromatic protons), δ=6.15–7.2 (d+dd, 2H, trans-olefin protons, J=36 Hz) δ=5.0–5.55 (m, 4H, 5β and 6aβ protons and the benzyl CH$_2$), δ=4.25 (s, 2h,COC$\underline{H}_2$N), δ=3.3 (t, 2H, NC$\underline{H}_2$, J=7 Hz), δ=0.9 (t, 3H, aliphatic methyl protons).

Example 10

The procedure described in Example 3 is followed but 5.7 g. (0.01 mole) of (−)-3,3aβ,4,5,6,6aβ-hexahydro-2-oxo-4β-[3-oxo-4-(N-propyl-benzyloxycarbonyl-amino)-1-transbuthenyl]-5α-(4-phenyl-benzoyloxy)-2H-cyclopenta[b]furane are used instead of (−)-3,3aβ,4,5,6-,6aβ-hexahydro-4β-[3-oxo-4(N-propyl-acetylamino)-1-trans-buthenyl]-5α-(4-phenyl-benzoyloxy)-2-oxo-2N-cyclopenta[b]furane. 4.4 g (76.5%) of (−)-3,3aβ,4,5,6-,6aβ-hexahydro-2-oxo-4-β-[(3S)-3-hydroxy-4-(N-propyl-benzyloxycarbonyl-amino)-1-trans-1-butenyl]-5α-(4-phenyl-benzoyloxy)-2H-cyclopenta[b]furane are obtained. R$_f$=0.39 (ethyl acetate/petroleum ether 3:2); R$_f$ for the compound of formula (IX) having an (R)-configuration =0.31 (ethyl acetate/petroleum ether 3:2). NMR (CDCl$_3$): δ=7.3–8.2 (m, 14H, aromatic protons), δ=5.7 (m, 2H, olefin protons); δ=4.9–5.45 (m, 4H, 5βand 6aβ and benzyl C$\underline{H}_2$ protons); δ=4.35 (m, 1H, C$\underline{H}$OH) δ=3–3.5 (m, 4H, C$\underline{H}_2$N).

Example 11

In a similar manner as described in Example 5 but substituting 3.0 g. (0.01 mol) of (−)-3,3aβ,4,5,6,6aβ-hexahydro-2-oxo-5α-hydroxy-4β-[(3S)-3-hydroxy-4-(N-propylbenzyloxycarbonyl-amino)-trans-1-buthenyl]-2H-cyclopenta[b]-furane for (−)-3,3aβ,4,5,6-,6aβ-hexahydro-2-oxo-5β-hydroxy-4β-[(3S)-3-hydroxy-4-(N-propyl-acetylamino)-trans-1-buthenyl)]-2N-cyclopenta[b]furane there are obtained 2.9 g. (97%) of (−)-3.3aβ,4,5,6,6aβ-hexahydro-2,5α-dihydroxy-4β-[(3S)-3-hydroxy-4-(N-propyl-benzyloxycarbonyl-amino)-trans-1-butenyl]-2H-cyclopenta[b]furane. R$_f$=0.09 (ethyl acetate/petroleum ether 2:1).

NMR (CDCl$_3$): δ=5.75 (m, 3H, olefin protons +OCHO protons) δ=5.2 (s, 2H, benzyl C$\underline{H}_2$, protons);

δ=4.25-4.8 (m, 3H, 5β, 6aβ and allyl C$\underline{H}$OH protons);
δ=3-3.5 (m, 4H, C$\underline{H}_2$N).

Example 12

Employing the procedure substantially as described in Example 6 but substituting 3.0 g. (0.01 mole) of (−)-3,3aβ-4,5,6,6aβ-hexahydro-2,5α-dihydroxy-4β-[(3S)-3-hydroxy-4-(N-propyl-benzyloxycarbonyl-amino)-1-trans-buthenyl]-2H-cyclopenta[b]furane for (−)-3,3aβ,4,5,6,6aβ-hexahydro-2,5α-dihydroxy- 4β-[(3S)-3-hydroxy-4(N-propyl-acetylamino)-trans-1-butenyl]-2H-cyclopenta[b]furane there are obtained 3.17 g. (65%) of (+)-9α,11α,15(S)-trihydroxy-16(N-propyl-benzyloxycarbonyl-amino)-17,18,19,20-tetranor-5-cis-13-transprostadienic acid.

$R_f$ =0.28 (benzene/dioxane/acetic acid 20:20:1). NMR (CDCl$_3$): δ=5.6 and δ=5.4 (m, 2H+2H, trans and cis olefin protons), δ=5.15 (s, 2H, benzyl C$\underline{H}_2$ protons), δ=3.95; 4.1 and 4.3 (1-1m, 3H, 9-OC$\underline{H}$, a 11-OC$\underline{H}$ and a 15-allyl OC$\underline{H}$ protons) δ=3-3.5(m, 4$\underline{H}$, C$\underline{H}_2$N), δ=0.85 (t, 3H, terminal methyl protons).

What is claimed is:

1. An optically active compound of the formula

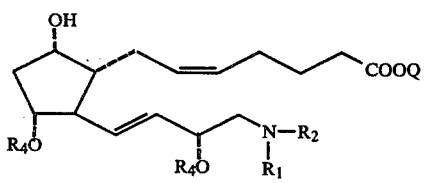

(XII)

or a racemate thereof, wherein

R$_1$ is alkanoyl of one to 4 carbon atoms, alkanoyl of one to 4 carbon atoms substituted with halogen or benzyloxycarbonyl;

R$_2$ is alkyl of one to 4 carbon atoms;

R$_4$ is hydrogen; and

Q is hydrogen or a pharmaceutically acceptable non-toxic cation.

2. A compound according to claim 1, wherein R$_1$ is alkanoyl of one to 4 carbon atoms or benzyloxycarbonyl; and R$_2$ is alkyl of one to 3 carbon atoms.

3. (+)-9α,11α,15(S)-trihydroxy-16-(N-propyl-acetylamino)-17,18,19,20-tetranor-5-cis-13-trans-prostadienic acid.

4. (+)-9α,11,15(S)-trihydroxy-16(N-propyl-benzyloxycarbonyl-amino)-17,18,19,20-tetranor-5-cis-13-transprostadienic acid.

5. A pharmaceutical composition for regulating gastric secretion and preventing the formation of thromboses, said composition comprising a therapeutically effective amount of a compound according to claim 1 and a pharmaceutical solid or liquid carrier therefor.

6. A pharmaceutical composition for regulating gastric secretion and preventing the formation of thromboses, said composition comprising a therapeutically effective amount of the compound according to claim 3 and a pharmaceutical solid or liquid carrier therefor.

7. A pharmaceutical composition for regulating gastric secretion and preventing the formation of thromboses, said composition comprising, in unitary dosage form, a therapeutically effective amount of a compound according to claim 1 and a pharmaceutical carrier therefor.

8. A pharmaceutical composition for regulating gastric secretion and preventing the formation of thromboses, said composition comprising a therapeutically effective amount of the compound according to claim 4 and a pharmaceutical solid or liquid carrier therefor.

* * * * *

UNITED STATES PATENT AND TRADEMARK OFFICE
CERTIFICATE OF CORRECTION

PATENT NO. : 4,191,774
DATED : March 4, 1980
INVENTOR(S) : Szekely et al.

It is certified that error appears in the above—identified patent and that said Letters Patent is hereby corrected as shown below:

Column 4, line 66: "agnets" should read -- agents --.

Column 5, line 52: "R/cl" should read -- $R_1^!Cl$ --.

Column 7, line 27: "(V1I)" should read -- (XII) --.

Column 8, line 50: "Y=4.9-55" should read -- $\delta$=4.9-55 --.

Column 9, line 33: "Y=4.45" should read -- $\delta$=4.45 --.

Column 10, line 68: "$\alpha$°C" should read -- 60°C

Column 12, line 22: "3a$\beta$-4" should read -- 3a$\beta$,4 --.

Column 12, line 30: "2h" should read -- 2H --.

Signed and Sealed this

Fifteenth Day of September 1981

[SEAL]

Attest:

GERALD J. MOSSINGHOFF

Attesting Officer    Commissioner of Patents and Trademarks